United States Patent [19]

Zweifel et al.

[11] 4,197,133
[45] Apr. 8, 1980

[54] PHOTO-CURABLE COMPOSITIONS OF MATTER CONTAINING BIS-AZIDOPHTHALIMIDYL DERIVATIVES

[75] Inventors: Hans Zweifel, Basel; Vratislav Kvita, Muttenz, both of Switzerland

[73] Assignee: Ciba-Geigy Corporation, Ardsley, N.Y.

[21] Appl. No.: 948,856

[22] Filed: Oct. 5, 1978

[30] Foreign Application Priority Data

Oct. 14, 1977 [CH] Switzerland ............... 12581/77

[51] Int. Cl.² .................. G03C 1/68; G03C 1/52
[52] U.S. Cl. .................. 430/195; 260/326 N; 260/349; 430/286; 430/283
[58] Field of Search ............. 96/91 N, 115 R, 35.1; 260/326 N, 349

[56] References Cited

U.S. PATENT DOCUMENTS

| | | | |
|---|---|---|---|
| 2,852,379 | 9/1958 | Hepher et al. | 96/91 N |
| 2,940,853 | 6/1960 | Sagura et al. | 96/91 N |
| 3,287,128 | 11/1966 | Lugasch | 96/91 N |
| 3,749,713 | 7/1973 | Clecak et al. | 96/115 R |
| 3,812,162 | 5/1974 | Clecak et al. | 260/349 |
| 3,856,531 | 12/1974 | Grisdale et al. | 96/91 N |
| 4,092,345 | 5/1978 | Wolford et al. | 260/326 N |

FOREIGN PATENT DOCUMENTS

| | | | |
|---|---|---|---|
| T 52852 | 12/1953 | Fed. Rep. of Germany | 96/91 N |
| 892811 | 3/1962 | United Kingdom | 96/91 N |
| 962557 | 7/1964 | United Kingdom | 96/91 N |
| 503855 | 4/1976 | U.S.S.R. | 96/91 N |

*Primary Examiner*—Won H. Louie, Jr.
*Attorney, Agent, or Firm*—Luther A. R. Hall

[57] ABSTRACT

The compositons of matter according to the invention consist of at least one polymeric compound and at least one compound of the formula I

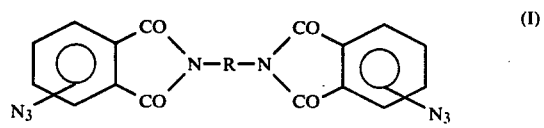

in which R is a divalent organic radical. The weight ratio of polymer to compound of the formula I is about 9:1 to 1:4.

The compounds of the formula I and thus also the compositions of matter are photo-curable (-crosslinkable). They are superior to known systems in respect of heat stability and oxidation resistance, while possessing photosensitivity which is equally as good.

14 Claims, No Drawings

PHOTO-CURABLE COMPOSITIONS OF MATTER CONTAINING BIS-AZIDOPHTHALIMIDYL DERIVATIVES

The invention relates to novel photo-curable compositions of matter containing bis-azidophthalimidyl derivatives and to their use for photo-crosslinking, especially for making reproductions.

The literature discloses that azido-phenyl derivatives, such as 4,4'-diazidostilbene, the disodium salt of 4,4'-diazidostilbene-2,2'-disulphonic acid, 4,4'-diazidobenzophenone, 4,4'-diazidochalkone, 2,6-di-(4'azidobenzal)-cyclohexanone, 2,6-di-(4'-azidobenzal)-4-methylcyclohexanone, 4,4'-diazidobenzalacetone and bis-(4'-azidocinnamylidene)-cyclopentanone, are suitable as sensitisers for polymers for phototechnical purposes, for example in so-called photoresists, or as photosensitive components in colloid layers, such as gelatin or caseine, for the production of so-called tanned images in photography, or in reprographic processes (cf., for example, U.S. Pat. No. 2,852,379, 2,940,853 and 3,749,713, German Patent specification No. 752,852, Russian Patent specification No. 503,855 and British Patent Specification No. 892,811).

These previously known azido-phenyl derivatives have disadvantages, since the heat stability and oxidation resistance of the compounds, or of mixtures containing these compounds, is not entirely satisfactory.

It was therefore the object of the invention to provide photo-curable systems which have improved heat stability and oxidation resistance, whilst possessing photosensitivity as good as that of compositions of matter which contain the abovementioned known substances.

The invention thus relates to photo-curable (-crosslinkable) compositions of matter which contain at least one polymeric compound and at least one compound of the formula I

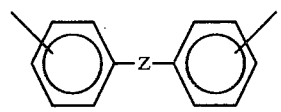
(I)

in which R is unsubstituted or substituted alkylene having 2-12 C atoms, unsubstituted or substituted phenylene, naphthylene, biphenylene, cyclohexylene or dicyclohexylmethane or an unsubstituted or substituted

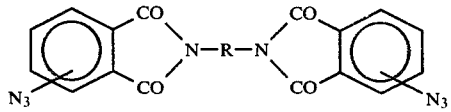

group and Z is —O—, —S—, —SO$_2$—, —CH$_2$—, —CO—,

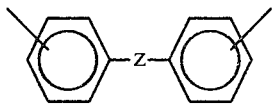

the weight ratio of the polymeric compound to the compound of the formula I being about 9:1 to 1:4.

Alkylene groups R can be straight-chain or branched and can be substituted, for example by one or more phenyl groups, cycloalkyl groups having 5-8 C atoms or aralkyl groups having 7 or 8 C atoms. Preferred substituted alkylene groups R are those which are substituted by one or two phenyl groups or by one or two cycloalkyl or aralkyl groups of the type defined, such as the cyclopentyl, cyclohexyl or cyclooctyl group or the benzyl group.

Examples of such alkylene groups R are the 1,2-ethylene, 1,3- or 1,2-propylene, 1,4- or 1,3-butylene, pentamethylene, hexamethylene, 2-methyl-4-dimethylhexane, 2-dimethyl-4-methylhexane, 1,10-dicyclohexyldecane, 1,10-dicyclooctyldecane, 1,10-diisopropyldecane, 1,1,10,10-tetramethyldecane, 1,10-diethyl-1,10-dimethyldecane, octamethylene, decamethylene and dodecamethylene groups.

Unsubstituted straight-chain or branched alkylene groups having 2-12 and especially 2-10 C atoms are preferred.

Phenylene, naphthylene, biphenylene, cyclohexylene or dicyclohexylmethane groups R and

groups R can also be substituted, for example by alkyl groups having 1-4 C atoms, —OH, —COO$^-$M$^+$ or —SO$_3^-$M$^+$ groups, in which M$^+$ is a hydrogen ion, an alkali metal cation, the pyridinium cation or

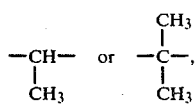

$X_1$ and $X_2$ independently of one another are hydrogen or alkyl having 1-12 C atoms and $X_3$ is hydrogen, alkyl having 1-12 C atoms or benzyl. Alkyl groups $X_1$, $X_2$ and $X_3$ can be straight-chain or branched. Preferably, they are straight-chain alkyl groups having 1-4 C atoms. The said groups R can have several substituents of the type mentioned on each ring, but advantageously are substituted by only one of the said groups per ring. Suitable alkyl substituents are, in particular, methyl and ethyl. If M$^+$ is a

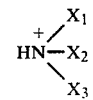

group, $X_1$ and $X_2$ are preferably alkyl groups having 1-4 C atoms and $X_3$ is an alkyl group having 1-4 C atoms or the benzyl group.

Preferred substituents —COO$^-$M$^+$ or —SO$_3^-$M$^+$ are those in which M$^+$ is a hydrogen ion, an alkali metal cation or a benzyldialkylammonium or trialkylammonium cation having 1-4 C atoms in each alkyl moiety. Particularly preferentially, M$^+$ is a hydrogen ion or a sodium or potassium cation.

Phenylene, naphthylene, biphenylene, cyclohexylene and dicyclohexylmethane groups or

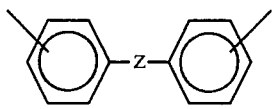

groups are preferably unsubstituted. Preferred bridge members Z are —O—, —SO$_2$— and —CH$_2$—.

The N$_3$ groups are preferably each bonded to the benzene ring in the 3-position.

Preferred compositions of matter are those in which the weight ratio of the polymeric compound to the compound of the formula I is about 9:1 to 1:1. The compositions of matter according to the invention can also contain several different compounds of the formula I. Particularly preferred compositions of matter are those which contain a compound of the formula I in which R is unsubstituted straight-chain or branched alkylene having 2–12 and especially 2–10 C atoms, unsubstituted phenylene or an unsubstituted diphenyl ether, diphenylmethane or diphenylsulphone radical.

Polymeric compounds which are photo-crosslinkable or -curable with the bis-azidophthalimidyl derivatives of the formula I can in principle be any known synthetic or natural polymers.

Examples of suitable polymers are: polyesters, polyester-amides, polyamides, polyamidoacids, polyamideamidoacids, polyimides, polyamidoimides, polyethers, polyamines, polyimines, polyurethanes, polyureas, polyurethane-ureas, polycarbonates, polycondensates based on phenol-formaldehyde, polysaccharides, gelatin or polymers which are obtained by homopolymerisation or copolymerisation of monomers containing reactive C=C double bonds.

Some preferred categories of polymers are listed below.

1. Polyamides, polyamidoacids, polyamide-amidoacids, polyesters and polyester-amides which contain identical or different recurring structural units of the formula II or III

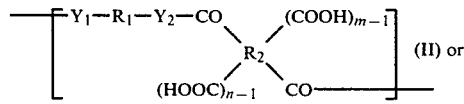

and the corresponding cyclised derivatives (polyimides and polyamidoimides);

2. Polyurethanes, polyureas and polyurethane-ureas which contain identical or different recurring structural units of the formula IV

3. Polyamines which contain identical or different recurring structural units of the formula V or VI

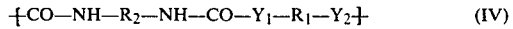
or

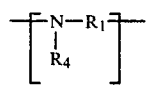

4. Polycarbonates which contain identical or different recurring structural units of the formula VII

5. Polyethers which contain recurring structural units of the formulae VIII, IX or X

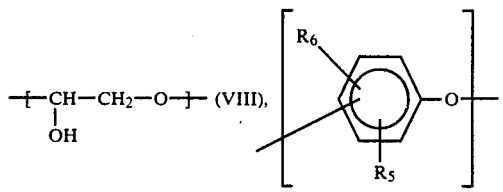

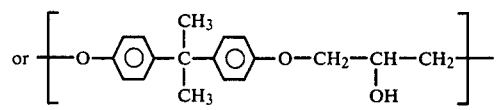

6. Phenol-formaldehyde condensation products (novolacs) which contain recurring structural units of the formula XI

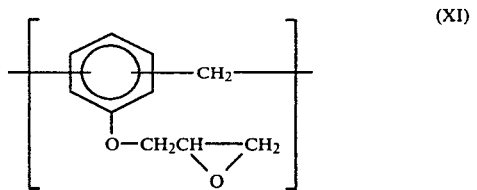

7. Homopolymers or copolymers of ethylenically unsaturated monomers which contain identical or different recurring structural units of the formula XII

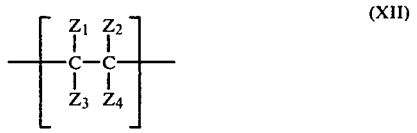

and

8. Cyclised isoprene polymers.

In the above formulae II to XII, m and n independently of one another are 1 or 2, Y$_1$ and Y$_2$ independently of one another are —O— or —NH—, R$_1$ is an aliphatic radical having at least 2 C atoms or a cycloaliphatic, aralphatic, carbocyclic-aromatic or heterocyclic-aromatic radical, R$_2$ is an aliphatic radical having at least 2 C atoms or a cycloaliphatic, carbocyclic-aromatic or heterocyclic-aromatic radical, R$_3$ is an aliphatic radical having at least 2 C atoms, R$_4$ is alkyl having 1–4 C atoms, cycloalkyl having 5–7 C atoms, aralkyl having 7 or 8 C atoms or aryl having 6–10 C atoms, R$_5$ and R$_6$ independently of one another are hydrogen or methyl, Z$_1$ and Z$_3$ are each hydrogen, Z$_2$ is hydrogen, chlorine or methyl and Z$_4$ is hydrogen, methyl, chlorine, —CN, —COOH, —CONH$_2$, phenyl, methylphenyl, methoxyphenyl, cyclohexyl, pyridyl, imidazolyl, pyrrolidonyl, —COO—alkyl having 1–12 C atoms in the alkyl moiety, —COO—phenyl,

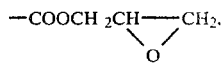

—COO—alkyl—OH having 1-3 C atoms in the alkyl,

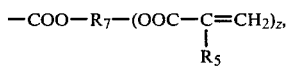

in which $R_7$ is a straight-chain or branched saturated aliphatic radical having 1-10 C atoms, $R_5$ is hydrogen or methyl and z is an integer from 1 to 3, or —OCO—alkyl having 1-4 C atoms in the alkyl, —OCO—phenyl, —CO—alkyl having 1-3 C atoms in the alkyl, alkoxy having 1-6 C atoms, phenoxy, —CH=CH$_2$ or

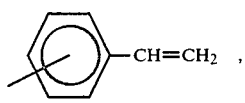

or $Z_1$ and $Z_2$ are each hydrogen and $Z_3$ and $Z_4$ together are the

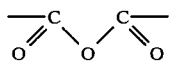

group or are each —COOH or —COO—alkyl having 1-6 C atoms in the alkyl.

Aliphatic radicals $R_1$, $R_2$ or $R_3$ are, in particular, straight-chain or branched alkylene groups having 2-12 C atoms, and the alkylene chain can also be interrupted by hetero-atoms, such as oxygen, sulphur or nitrogen atoms. Such groups are preferably unsubstituted alkylene groups having 2-10 C atoms.

Cycloaliphatic radicals $R_1$ or $R_2$ are, for example, the 1,3- or 1,4-cyclohexylene, 1,4-bis-(methylene)-cyclohexane or dicyclohexylmethane group, whilst araliphatic radicals $R_1$ are, in particular, 1,3-, 1,4- and 2,4-bis-alkylenebenzene, 4,4'-bis-alkylene-diphenyl and 4,4'-bis-alkylene-diphenyl-ether groups.

Carbocyclic-aromatic and heterocyclic-aromatic radicals $R_1$ and $R_2$ can also be substituted, for example by alkyl or alkoxy groups having 1-4 C atoms or by halogen atoms, such as flourine, chlorine or bromine.

Carbocyclic-aromatic radicals $R_1$ and $R_2$ can be monocyclic, fused polycyclic or non-fused bicyclic, and in the latter case the aromatic nuclei are preferably bonded to one another via a bridge member. Preferred carbocyclic-aromatic radicals $R_1$ are: the 1,3- and 1,4-phenylene group and the 4,4'-diphenylmethane, 4,4'-diphenyl ether and 4,4'-diphenylsulphone radical. Preferred carbocyclic-aromatic radicals $R_2$ are the 1,3- and 1,4-phenylene group, benzenetriyl and benzenetetrayl groups and also the benzophenone ring system.

Carbocyclic-heterocyclic radicals $R_1$ and $R_2$ are, in particular, 5-membered or 6-membered ring systems containing O, N and/or S.

Mixtures of different polymers can also be used.

Preferred polymers are polyethers which contain recurring structural units of the formula X, phenolformaldehyde condensation products which contain recurring structural units of the formula XI, cyclised isoprene polymers and homopolymers or copolymers which contain identical or different structural units of the formula XII, such as polyolefins, for example polyethylene and polyisoprene, polyvinyl chloride, polyvinylidene chloride and copolymers thereof with other vinyl monomers, for example vinyl acetate, polyvinyl acetate, styrene polymers, acrylic polymers, especially poly(alkyl acrylates) and poly(alkyl methacrylates), and also maleic anhydride polymers.

Particularly preferred polymers are polyvinyl chloride, polystyrene, poly(alkyl acrylates) and poly(alkyl methacrylates) having 1-8 C atoms in the alkyl moiety, cyclised isoprene polymers, copolymers of maleic anhydride and vinyl ethers or α-olefins, such as methyl vinyl ether or ethylene, as well as polyethers which contain recurring structural units of the formula X.

The compositions of matter according to the invention can contain, for example, known curing agents, glidants, adhesion promoters and, if desired, also triplet sensitisers, such as phenol, benzophenone and the like, as further additives.

The abovementioned polymers can be prepared by methods known per se, by polycondensation, polyaddition or polymerisation.

Particularly preferred compositions of matter according to the invention are the following five:

(1.) A composition of matter which preferably contains a copolymer of maleic anhydride and ethylene as the polymeric compound and 4,4'-bis-(3-azidophthalimidyl)-diphenyl ether as the compound of the formula I, the mixture preferably containing about 50% by weight, based on the mixture of the two substances, of the polymeric compound.

(2.) A composition of matter which preferably contains a copolymer of maleic anhydride and methyl vinyl ether as the polymeric compound and 4,4'-bis-(3-azidophthalimidyl)-diphenylmethane as the compound of the formula I, the mixture preferably containing about 75% by weight, based on the mixture of the two substances, of the polymeric compound.

(3.) a composition of matter which preferably contains a polystyrene as the polymeric compound and 4,4'-bis-(3-azidophthalimidyl)-diphenylmethane as the compound of the formula I, the mixture preferably containing about 50% by weight, based on the mixture of the two substances, of the polymeric compound.

(4.) A composition of matter which preferably contains a cyclised polyisoprene as the polymeric compound and 3,3'-dimethyl-4,4'-bis-(3-azidophthalimidyl)-dicyclohexylmethane as the compound of the formula I, the mixture preferably containing about 35% by weight, based on the mixture of the two substances, of the polymeric compound.

(5.) A composition of matter which preferably contains a copolymer of maleic anhydride and methyl vinyl ether as the polymeric compound and 1,4-bis-(3-azidophthalimidyl)-benzene as the compound of the formula I, the mixture preferably containing about 50% by weight, based on the mixture of the two substances, of the polymeric compound.

The bis-azidophthalimidyl derivatives of the formula I can be prepared by reacting a compound of the formula XIII

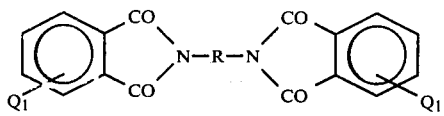

(XIII)

in which R is as defined under formula I and $Q_1$ is a halogen atom, such as chlorine, fluorine or bromine, or, preferably, the nitro group, in an inert organic solvent at a temperature between about 30° and 120° C., especially between about 70° and 100° C., with an azide of the formula XIV

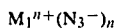 (XIV)

in which n is 1 or 2 and $M_1$ is an alkali metal cation, an alkaline earth metal cation or a quaternary ammonium cation.

$Q_1$ is preferably the nitro group.

A quaternary ammonium cation $M_1$ is, for example, a tetraalkylammonium cation or a benzyltrialkylammonium cation having 1–12 and especially 1–4 C atoms in each alkyl moiety, such as the tetramethylammonium cation and the trimethylbenzylammonium cation.

The azide of the formula XIV is advantageously employed in excess, for example in about 5–50% molar excess and preferably in about 10–30% molar excess.

Alkali metal azides, especially sodium azide, are preferably used. Suitable inert organic solvents for this reaction are, in particular, polar solvents, such as aliphatic alcohols having not more than 6 C atoms, dibenzyl ether and dialkyl ethers having 1–4 C atoms in each alkyl moiety, diethylene glycol dialkyl ethers and triethylene glycol dialkyl ethers having 1–4 C atoms in each alkyl moiety, aliphatic and aromatic nitriles, cyclic amides, N,N-dialkylamides of aliphatic monocarboxylic acids having 1–3 C atoms in the acid moiety, dialkyl sulphoxides, such as dimethylsulphoxide and diethylsulphoxide, hexamethylphosphoric acid triamide and tetrahydrothiophene dioxide.

The compounds of the formula I can also be prepared by reacting a compound of the formula XV

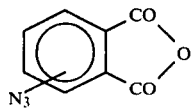 (XV)

with a diamine of the formula XVI $H_2N—R—NH_2$ (XVI)

to give a compound of the formula XVII

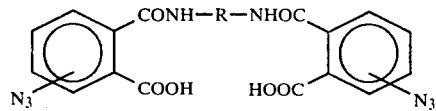 (XVII)

in which formulae R is as defined under formula I, and subsequently cyclising the compound of the formula XVII.

The reaction of the anhydrides of the formula XV with the diamines of the formula XVI is advantageously carried out in an organic medium, the reaction temperature being between about 0° C. and 120° C., depending on the nature of the reactants.

Suitable organic solvents are, in particular, aprotic solvents, such as aliphatic or aromatic hydrocarbons, which can be chlorinated, for example benzene, toluene, methylene chloride, chloroform, carbon tetrachloride, 1,2-dichloroethane and chlorobenzene; aliphatic and cycloaliphatic ketones, for example acetone, methyl ethyl ketone and cyclohexanone; cyclic ethers, such as tetrahydrofuran and dioxan; cyclic amides, such as N-methyl-2-pyrrolidone and N-acetyl-2-pyrrolidone; N,N-dialkylamides of aliphatic monocarboxylic acids having 1–3 C atoms in the acid moiety, such as N,N-dimethylformamide and N,N-dimethylacetamide, and dialkylsulphoxides.

The cyclisation of the compounds of the formula XVII can be carried out in a manner known per se, by chemical means, i.e. using known dehydrating agents, such as anhydrides of aliphatic monocarboxylic acids having 2–5 C atoms, in particular acetic anhydride. Depending on the nature of the reactants, the reaction conditions and the solvent used, the cyclisation can, especially at elevated temperatures, also be carried out without adding a dehydrating agent, the water formed advantageously being removed azeotropically.

The compounds of the formulae XIII to XVI are known or can be prepared in a manner known per se. Compounds of the formula XIII can be obtained, for example, by reacting 3- or 4-nitrophthalic anhydride, or the corresponding halogen compounds, with diamines of the formula XVI and subsequently cyclising the amidocarboxylic acids thus formed.

The compositions of matter according to the invention can be cured or crosslinked under the action of light, especially UV light, and are suitable, for example, for the manufacture of printing plates for the offset printing process, for the manufacture of photo-offset lacquers, for unconventional photography, for example for the production of so-called vesicular images, or for colouring polymer images, which after exposure and development are not easily visible, by means of suitable dyes, such as oil-soluble dyes or, if the polymer contains acid groups, such as carboxylic acid or sulphonic acid groups, cationic dyes. The compositions of matter according to the invention are used in particular as so-called photoresists for the manufacture of printed circuits by methods known per se. In these, the side of the conductive plate provided with the photosensitive layer is exposed through a negative transparency carrying the conductor image and is then developed, after which the unexposed areas of the layer are removed with developer fluid.

Exposure can be effected by means of sunlight, carbon arcs or xenon lamps, but is preferably carried out with mercury high pressure lamps.

The carriers can be coated with the photosensitive composition of matter by conventional techniques, for example by dipping methods, spraying, centrifugal coating, cascade coating and curtain coating or so-called roller coating.

The compositions of matter according to the invention are generally used in the form of solutions or suspensions in suitable organic solvents or solvent mixtures, such as N,N-dialkylamides of aliphatic monocarboxylic acids, aliphatic or cyclic ketones or cyclic ethers of the abovementioned type.

EXAMPLE 1

An aluminium plate is coated with a solution of 3 g of 1,4-bis-(3-azidophthalimidyl)-butane and 5 g of a copolymer of maleic anhydride and ethylene ("EMA 21", a commercial product from Monsanto) in 72 ml of N,N-dimethylformamide, using a coating centrifuge (300 revolutions per minute). After drying the coating, the coated plate is exposed for 1 minute, through a line negative, to UV light (mercury high pressure lamp with a Pyrex filter in front of the lamp, wavelength greater than 320 nm). The exposed plate is then developed in 5 to 10% aqueous sodium bicarbonate solution, resulting in a relief image, corresponding to the line negative; if desired, the image can be dyed with a cationic dye.

EXAMPLES 2 TO 13

The following table lists further compositions of matter according to the invention with which reproductions can be produced on photosensitive plates in the manner described in Example 1.

Table

| Example | Composition Bis-azide of the formula I | Polymer | Per cent by weight Azide | Polymer |
|---|---|---|---|---|
| 2 | (diamine component = isomer mixture of 1,6-diamino-2-methyl-4-dimethylhexane and 1,6-diamino-2-dimethyl-4-methylhexane) | $[-CH_2-CH_2-CH-CH-]$ with anhydride | 37,5 | 62,5 |
| 3 | bis-azidophthalimidyl with -N-C6H4-O-C6H4-N- bridge | " | 50 | 50 |
| 4 | bis-azidophthalimidyl with -N-C6H4-CH2-C6H4-N- bridge | " | 33,5 | 66,5 |
| 5 | " | $[-CH_2-CH(OCH_3)-CH-CH-]$ with anhydride (Gantrez 119)* | 26 | 74 |
| 6 | N—(CH2)6—N bis-azidophthalimide | $[-CH_2-CH_2-CH-CH-]$ with anhydride | 50 | 50 |
| 7 | N—CH(CH3)—(CH2)8—CH(CH3)—N bis-azidophthalimide (diamine component according to German Offenlegungsschrift 2,549,403) | " | 50 | 50 |

Table-continued

| Example | Composition Bis-azide of the formula I | Polymer | Per cent by weight A-zide | Polymer |
|---|---|---|---|---|
| 8 | 3-azido-phthalimidyl–C₆H₄–CH₂–C₆H₄–phthalimidyl-3-azido | [–CH(C₆H₅)–CH₂–]ₙ (polystyrene) | 50 | 50 |
| 9 | bis(3-azidophthalimidyl) linked via N–(4-methylcyclohexyl)–CH₂–(4-methylcyclohexyl)–N | Isoprene Type I* J. Pol. Scie.A-1 (Vol. 10) 1839–1850 (1972) | 64.94 | 35 |
| 10 | bis(3-azidophthalimidyl) linked via N–C₆H₄–C₆H₄–N (biphenyl) | [–CH₂–CH(OCH₃)–CH(–C(=O)–O–C(=O)–)CH–]ₙ | 50 | 50 |
| 11 | bis(3-azidophthalimidyl) linked via N–C₆H₄–N (p-phenylene) | " | 50 | 50 |
| 12 | bis(3-azidophthalimidyl) linked via N–C₆H₄–SO₂–C₆H₄–N | " | 50 | 50 |
| 13 | 2-azido-6-COOH-C₆H₃–C(=O)–NH–(CH₂)₄–NH–C(=O)–C₆H₃-6-COOH-2-azido | [–CH₂–CH₂–CH(–C(=O)–O–C(=O)–)CH–]ₙ | 40 | 60 |

*"Gantrez 119 AN", a commercial product from General Aniline & Film Corporation

EXAMPLE 14

1.35 g of 4,4'-bis-(3-azidophthalimidyl)-diphenyl ether are dissolved in 100 ml of cyclohexane and the solution is then mixed, with the exclusion of light, with 100 g of a 2.5% solution of a synthetic isoprene polymer ("Cariflex IR 309", a commercial product from Shell AG) in chlorobenzene.

A copper-laminated epoxy plate is coated with this solution and the coating is dried in vacuo at 40° C. and then exposed, through a negative, to UV light ($\lambda$ greater than 320 nm). After development with 1,1,1-trichloroethane, an image corresponding to the negative appears.

EXAMPLE 15

With the exclusion of light, 4.0 g of 4,4'-bis-(3-azidophthalimidyl)-diphenyl ether are dissolved in 27 ml of cyclohexanone and the solution is then mixed with 6.0 g of a mixture consisting of 99.5 parts by weight of an epoxide resin (reaction product of 72.82 parts by weight of epichlorohydrin and 27.18 parts by weight of 2,2-bis-(p-hydroxyphenyl)-propane, epoxide content 1.2 to 1.4 epoxide equivalents/kg), 4.8 parts by weight of a curing agent (o-tolylbiguanide obtained from 59.4 parts by weight of o-toluidine and 40.6 parts by weight of dicyandiamide) and 0.5 part by weight of an agent which improves the flow and adhesion characteristics of the coating composition ("Modaflow", a commercial product from Monsanto) in 16 ml of N,N-dimethylformamide. A copperlaminated epoxy plate is coated with the resulting solution and the coating is dried in vacuo at 40° C. and then exposed, through a negative, to UV light ($\lambda$ greater than 320 nm). After development with 1,1,1-trichloroethane, an image corresponding to the negative is obtained.

The bis-azidophthalimides used in the above examples can be prepared as follows:

(a) 1,4-Bis-(3-azidophthalimidyl)-butane

A mixture of 21.3 g (0.048 mol) of 1,4-bis-(3-nitrophthalimidyl)-butane and 7.2 g (0.11 mol) of sodium azide in 225 ml of N,N-dimethylformamide is heated for 18 hours at 80° C. and is then evaporated in vacuo at the same temperature. The residue is stirred with 200 ml of water and the mixture is acidified with 1 ml of concentrated hydrochloric acid. The resulting suspension of the product is filtered with suction and the filter residue is washed with 20 ml of water and dried for 24 hours at 80° C. in a drying cabinet. 20.4 g (98.8% of theory) of 1,4-bis-(3-azidophthalimidyl)-butane are obtained; melting point 162° C. (with decomposition).

The 1,4-bis-(3-nitrophthalimidyl)-butane can be prepared as follows: 8.1 g (0.042 mol) of 3-nitrophthalic anhydride are suspended in 15 ml of acetic acid in an autoclave, 1.76 g (0.02 mol) of 1,4-diaminobutane in 15 ml of toluene are added and the mixture is stirred for 6 hours at 120° C. The resulting thick precipitate is filtered off with suction and dried for 24 hours at 120° C./100 mm Hg. 7.8 g (90% of theory) of 1,4-bis-(3-nitrophthalimidyl)-butane are obtained; melting point 245° C.

(b) Isomer mixture of 1,6-bis-(3-azidophthalimidyl)-2-methyl-4-dimethylhexane and 1,6-bis-(3-azidophthalimidyl)-2-dimethyl-4-methylhexane The method of preparation is analogous to that described under (a), 20.3 g (0.04 mol) of an isomer mixture of 1,6-bis-(3-nitrophthalimidyl)-2-methyl-4-dimethylhexane and 1,6-bis-(3-nitrophthalimidyl)-2-dimethyl-4-methylhexane and 7.78 g (0.104 mol) of sodium azide being used. An isomer mixture is obtained in the form of a finely divided glassy mass which deliquesces on heating and decomposes at 180° C., with foaming.

(c) 4,4'-Bis-(3-azodiphthalimidyl)-diphenylmethane

The method of preparation is analogous to that described under (a), 9.5 g (0.017 mol) of 4,4'-bis-(3-nitrophthalimidyl)-diphenylmethane and 2.8 g (0.044 mol) of sodium azide being used. Yield: 81.5% of theory; melting point 182° C. (with decomposition).

(d) 4,4'-Bis-(3-azidophthalimidyl)-diphenyl ether

The method of preparation is analogous to that described under (a), 22 g (0.04 mol) of 4,4'-bis-(3-nitrophthalimidyl)-diphenyl ether and 7.78 g (0.104 mol) of sodium azide being used. Yield: 88.5% of theory; melting point 185° C. (with decomposition).

(e) 1,6-Bis-(3-azidophthalimidyl)-hexane

The method of preparation is analogous to that described under (a), 20 g (0.043 mol) of 1,6-bis-(3-nitrophthalimidyl)-hexane and 7.2 g (0.111 mol) of sodium azide being used. Yield: 78% of theory; melting point 147° C. (with decomposition).

(f) 1,10-Bis-(3-azidophthalimidyl)-1,10-dimethyldecane

The method of preparation is analogous to that described under (a), 8 g (0.014 mol) of 1,10-bis-(3-nitrophthalimidyl)-1,10-dimethyldecane and 2.36 g (0.035 mol) of sodium azide being used. Yield: 80% of theory. The reaction product is obtained in the form of a viscous oil.

What is claimed is:

1. A photo-curable composition of matter which contains at least one polymeric compound and at least one compound of the formula I

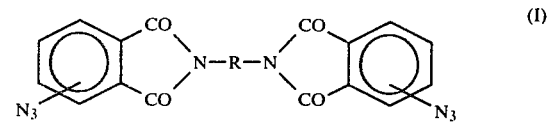

in which R is unsubstituted or substituted alkylene having 2 to 12 C atoms, unsubstituted or substituted phenylene, naphthylene, biphenylene, cyclohexylene or dicyclohexylmethane or an unsubstituted or substituted

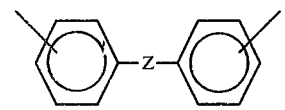

group and Z is —O—, —S—, —SO$_2$—, —CH$_2$—, —CO—,

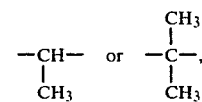

the weight ratio of the polymeric compound to the compound of the formula I being about 9:1 to 1:4.

2. A composition of matter according to claim 1, wherein the weight ratio of the polymeric compound to the compound of the formula I is about 9:1 to 1:1.

3. A composition of matter according to claim 1, in which the N$_3$ groups in the compound of the formula I are each bonded to the benzene ring in the 3-position.

4. A composition of matter according to claim 1, in which R in formula I is alkylene having 2 to 12 C atoms, which is unsubstituted or substituted by one or two phenyl groups, cycloalkyl groups having 5 to 8 C atoms or aralkyl groups having 7 or 8 C atoms, or phenylene, naphthylene, biphenylene, cyclohexylene, dicyclohexylmethane or

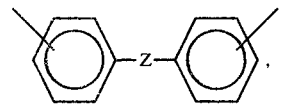

which are unsubstituted or substituted, per ring, by one alkyl group having 1 to 4 C atoms, one —OH, —COO$^-$M$^+$ or —SO$_3$$^-$M$^+$ group, Z is as defined under formula I, M$^+$ is a hydrogen ion, an alkali metal cation, the pyridinium cation or

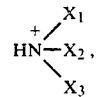

X$_1$ and X$_2$ independently of one another are hydrogen or alkyl having 1 to 12 C atoms and X$_3$ is hydrogen, alkyl having 1 to 12 C atoms or benzyl.

5. A composition of matter according to claim 1, in which R in formula I is unsubstituted straight-chain or branched alkylene having 2 to 12 C atoms, unsubstituted phenylene or an unsubstituted diphenyl-ether, diphenylmethane or diphenylsulphone radical.

6. A composition of matter according to claim 1, in which the polymeric compound is a polyester, a polyesteramide, a polyamide, a polyamidoacid, a polyamideamidoacid, a polyimide, a polyamidoimide, a polyether, a polyamine, a polyimine, a polyurethane, a polyurea, a polyurethane-urea, a polycarbonate, a polycondensate based on phenol-formaldehyde, a polysaccharide, gelatin or a polymer which is obtained by homopolymerisation or copolymerisation of monomers containing reactive C=C double bonds.

7. A composition of matter according to claim 1, wherein the polymeric compound is a polyether which contains recurring structural units of the formula X

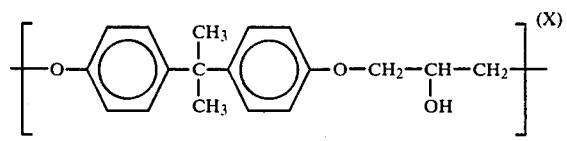

a phenol-formaldehyde condensation product which contains recurring structural units of the formula XI

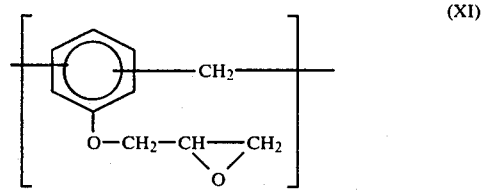

a homopolymer or copolymer of ethylenically unsaturated monomers which contains identical or different recurring structural units of the formula XII

or a cyclised isoprene polymer, and, in formula XII, $Z_1$ and $Z_3$ are each hydrogen, $Z_2$ is hydrogen, chlorine or methyl and $Z_4$ is hydrogen, methyl, chlorine, —CN, —COOH, —CONH$_2$, phenyl, methylphenyl, methoxyphenyl, cyclohexyl, pyridyl, imidazolyl, pyrrolidonyl, —COO—alkyl having 1 to 12 C atoms in the alkyl moiety, —COO—phenyl,

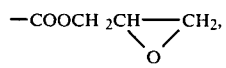

—COO—alkyl—OH having 1 to 3 C atoms in the alkyl,

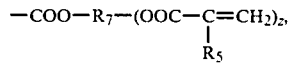

in which $R_7$ is a straight-chain or branched saturated aliphatic radical having 1 to 10 C atoms, $R_5$ is hydrogen or methyl and z is an integer from 1 to 3, or —OCO—alkyl having 1 to 4 C atoms in the alkyl, —OCO—phenyl, —CO—alkyl having 1 to 3 C atoms in the alkyl, alkoxy having 1 to 6 C atoms, phenoxy, —CH=CH$_2$ or

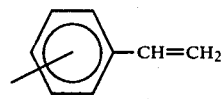

or $Z_1$ and $Z_2$ are each hydrogen and $Z_3$ and $Z_4$ together are the

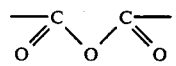

group or are each —COOH or —COO—alkyl having 1 to 6 C atoms in the alkyl.

8. A composition of matter according to claims 1 and 7, wherein the polymeric compound is a polyvinyl chloride, a polystyrene, a poly(alkyl acrylate) or poly(alkyl methacrylate) having 1 to 8 C atoms in the alkyl moiety, a cyclised isoprene polymer, a copolymer of maleic anhydride and methyl vinyl ether or ethylene or a polyether which contains recurring structural units of the formula X.

9. A composition of matter according to claim 1, which contains a copolymer of maleic anhydride and ethylene as the polymeric compound and 4,4'-bis-(3-azidophthalimidyl)-diphenyl ether as the compound of the formula I, the mixture containing about 50% by weight, based on the mixture of the two substances, of the polymeric compound.

10. A composition of matter according to claim 1, which contains a copolymer of maleic anhydride and methyl vinyl ether as the polymeric compound and 4,4'-bis-(3-azidophthalimidyl)-diphenylmethane as the compound of the formula I, the mixture containing about 75% by weight, based on the mixture of the two substances, of the polymeric compound.

11. A composition of matter according to claim 1, which contains a polystyrene as the polymeric compound and 4,4'-bis-(3-azidophthalimidyl)-diphenylmethane as the compound of the formula I, the mixture containing about 50% by weight, based on the mixture of the two substances, of the polymeric compound.

12. A composition of matter according to claim 1, which contains a cyclised polyisoprene as the polymeric compound and 3,3'-dimethyl-4,4'-bis-(3-azidophthalimidyl)-dicyclohexylmethane as the compound of the formula I, the mixture containing about 35% by weight, based on the mixture of the two substances, of the polymeric compound.

13. A composition of matter according to claim 1, which contains a copolymer of maleic anhydride and methyl vinyl ether as the polymeric compound and 1,4-bis-(3-azidophthalimidyl)-benzene as the compound of the formula I, the mixture containing about 50% by weight, based on the mixture of the two substances, of the polymeric compound.

14. A composition according to claim 5 wherein R is alkylene of 2 to 10 carbon atoms.

* * * * *